(12) United States Patent
Mikos et al.

(10) Patent No.: US 6,306,821 B1
(45) Date of Patent: Oct. 23, 2001

(54) FUNCTIONALIZED POLY(PROPYLENE FUMARATE) AND POLY(PROPYLENE FUMARATE-CO-ETHYLENE GLYCOL)

(75) Inventors: Antonios G. Mikos; Seongbong Jo, both of Houston, TX (US)

(73) Assignee: Wm. Marsh Rice University, Houston, TX (US)

( * ) Notice: Subject to any disclaimer, the term of this patent is extended or adjusted under 35 U.S.C. 154(b) by 0 days.

(21) Appl. No.: 09/549,483

(22) Filed: Apr. 14, 2000

Related U.S. Application Data

(60) Provisional application No. 60/129,577, filed on Apr. 16, 1999, provisional application No. 60/146,991, filed on Aug. 3, 1999, provisional application No. 60/167,328, filed on Nov. 24, 1999, and provisional application No. 60/167,388, filed on Nov. 24, 1999.

(51) Int. Cl.$^7$ ................................. A23L 1/28; A23L 1/36; A23L 2/02; A23P 1/00; C08F 16/06
(52) U.S. Cl. ..................................... 514/2; 514/3; 514/23; 525/54.1; 525/54.2; 525/54.21; 525/54.23; 525/54.24; 525/54.26; 525/54.3; 525/54.31; 525/54.4; 525/54.44; 530/812; 530/815
(58) Field of Search .................... 514/2, 3, 23; 525/54.1, 525/54.2, 54.21, 54.23, 54.24, 54.26, 54.3, 54.31, 54.4, 54.44; 530/812, 815

(56) References Cited

U.S. PATENT DOCUMENTS

| | | | |
|---|---|---|---|
| 5,945,457 | 8/1999 | Plate et al. | 514/772.1 |
| 5,986,043 | 11/1999 | Hubbell et al. | 528/354 |
| 5,998,362 | 12/1999 | Feng et al. | 514/2 |
| 6,028,164 | 2/2000 | Loomis | 528/354 |

OTHER PUBLICATIONS

PCT International Search Report Dated Jul. 19, 2000 (4 p.).

*Primary Examiner*—Nathan M. Nutter
(74) *Attorney, Agent, or Firm*—Conley, Rose & Tayon, P.C.

(57) ABSTRACT

Poly(ethylene glycol) (PEG), a highly biocompatible hydrophilic polyether, is tethered to poly(propylene fumarate) (PPF), a biodegradable polyester. To avoid change in molecular weight distribution of PPF, end hydroxyl groups of PPF are reacted with bis-carboxymethyl PEG after being treated with thionyl chloride. New end carboxyl groups of the PEG-tethered PPF are further reacted with N-hydroxysuccinimide (NHS) in the presence of dicyclohexylcarbodiimide (DCC) to couple bioactive molecules. Glutamine and glycine-arginine-glycine-aspartic acid (GRGD) are attached to the PEG-tethered PPF in 50 mM phosphate buffer of pH of 7.4. The method is valuable for the preparation of a triblock copolymer with PEG end blocks and the coupling of biologically active molecules.

24 Claims, 7 Drawing Sheets

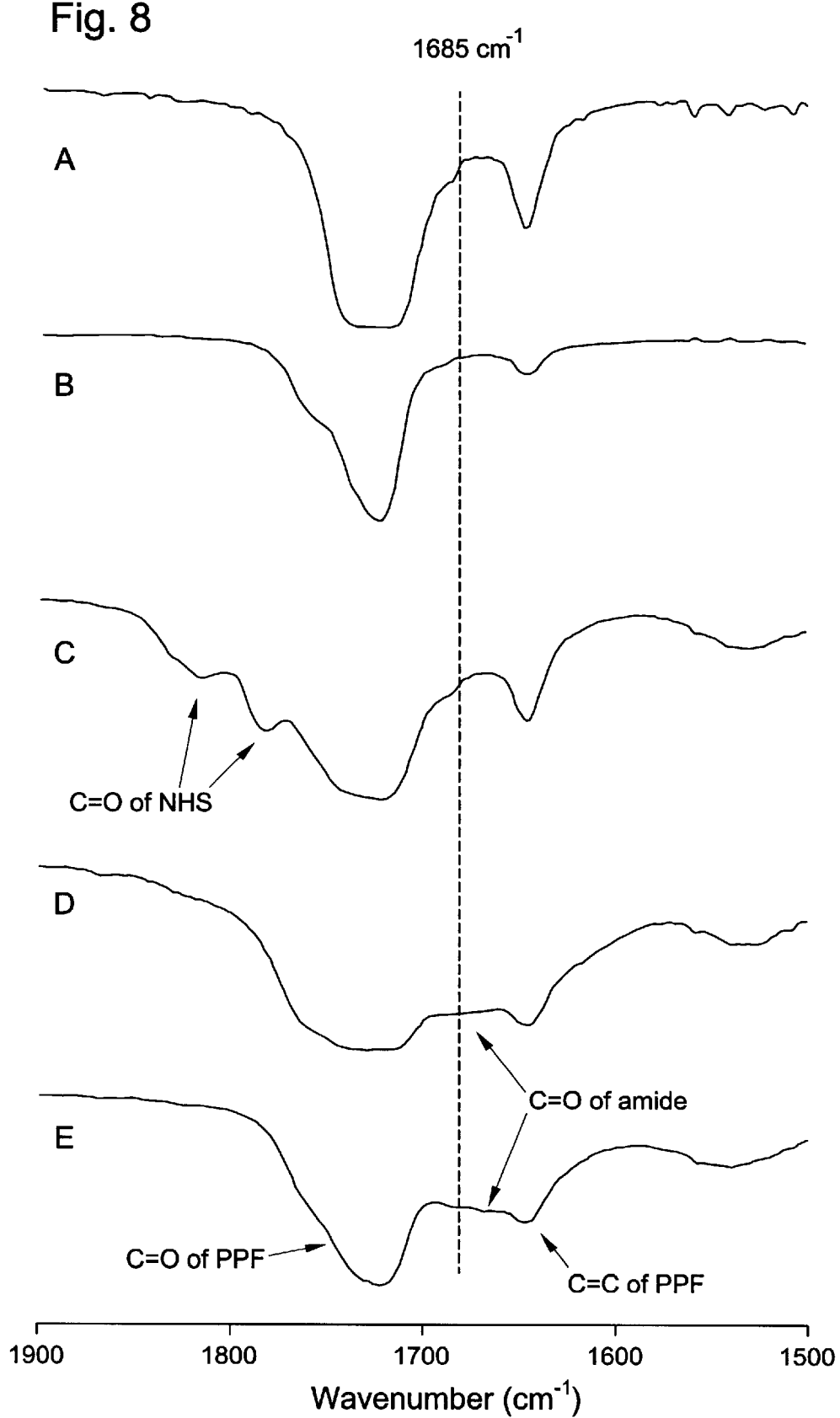

FUNCTIONALIZED POLY(PROPYLENE FUMARATE) AND POLY(PROPYLENE FUMARATE-CO-ETHYLENE GLYCOL)

RELATED CASES

The present case claims the benefit of U.S. provisional applications Ser. No. 60/129,577, filed Apr. 16, 1999, and entitled "Development of Biodegradable Bone Cement Based on Poly(Propylene Fumarate) and a Macromer," Ser. No. 60/146,991, filed Aug. 3, 1999, and entitled "Synthesis of Poly (Propylene Fumarate) by Acylation of Propylene Glycol in the Presence of a Proton Scavenger," Ser. No. 60/167,328, filed Nov. 24, 1999, and entitled "Preparation of an Injectable, in situ Polymerizable and Biodegradable Biomaterial Based On Poly(Propylene Fumarate) and Biodegradable Cross linking Reagents," and Ser. No.60/167,388, filed Nov. 24, 1999, and entitled "Injectable Biodegradable Polymer Composites Based on Poly(Propylene Fumarate) Cross linked with Poly(Ethylene Glycol)-Dimethacrylate and β-Tricalcium Phosphate," all of which are incorporated herein by reference.

STATEMENT REGARDING FEDERALLY SPONSORED RESEARCH OR DEVELOPMENT

This work was funded by the National Institutes of Health R01-AR44381 and R01-DE13031.

TECHNICAL FIELD OF THE INVENTION

This invention relates to a compound for replacing or reconstructing rigid or semi-rigid living tissue. More particularly, the present invention relates to a method for tethering PEG to PPF ends and for modifying the remaining carboxyl end groups of PEG-tethered PPF so they can be further modified with peptides, so as to form poly(propylene fumarate-co-peptide).

BACKGROUND OF THE INVENTION

In the field of tissue engineering, degradable biomaterials usually serve as a scaffold to provide mechanical support and a matrix for the ingrowth of new tissue. As new tissue forms on the scaffold, the biomaterial degrades until it is entirely dissolved. The degradation products are eliminated through the body's natural pathways, such as metabolic processes.

One example of the use of such biomaterials is as a temporary bone replacement. It is often desired to replace or reconstruct all or a portion of a living bone, such as when a bone has been broken or has been resected as a result of a bone tumor. In these instances, the missing bone can be replaced with a mechanical device, such as a pin, plate or the like, or it can be replaced with an implant that is designed to more closely resemble the original bone itself. Often these implants comprise biodegradable polymeric compounds or parts made from such compounds. It is contemplated that bone tissue will grow back into the pores of the implant and will gradually replace the entire implant as the implant itself is gradually degraded in the in vivo environment. For obvious reasons then, such implants should be biocompatible and non-toxic.

Poly(propylene fumarate) (PPF) is one such polymer. Poly(propylene fumarate) (hereinafter "PPF") is an unsaturated linear polyester that degrades in the presence of water into propylene glycol and fumaric acid, degradation products that are easily cleared from the human body by normal metabolic processes. Because the fumarate double bonds in PPF are reactive and cross link at low temperatures, it has potential to be an effective in situ polymerizable biomaterial. The high mechanical strength of cured PPF matrices and their ability to be cross linked in situ makes them especially suitable for orthopedic application. Another advantage of cured PPF matrices is that they biodegrade into non-toxic propylene glycol and fumaric acid. On the basis of these unique properties, PPF has been formulated as bone cement, an orthopaedic scaffold for bone tissue regeneration, and a drug delivery system.

Several PPF-based formulation methods have been evaluated by varying such parameters as the molecular weight of PPF and the choice of cross linking reagents. For example, U.S. Pat. No. 5,733,951 discloses a composite mixture incorporating P(PF), a cross linking monomer (N-vinyl pyrrolidone), a porogen (sodium chloride), and a particulate phase (β-tricalcium phosphate) that can be injected or inserted into skeletal defects of irregular shape or size.

To extend its application in biomedical science, PPF has been modified with polyethylene glycol (PEG), a highly flexible hydrophilic polyether, by transesterification. Incorporation of PEG into PPF decreases platelet adhesion on the material for cardiovascular application. Mechanical properties of a hydrogel made of poly(propylene fumarate-co-ethylene glycol) (P(PF-co-EG)) can be controlled by varying the ratio between hydrophilic PEG and hydrophobic PPF, as set out in concurrently filed application Ser. No. 09/550,372, entitled Poly(Propylene Fumarate) Cross Linked With Poly (Ethylene Glycol) incorporated herein by reference.

Despite advances in PPF technology, it is still desired to be able to modify PPF so as to increase its effectiveness for various bioactive purposes. For example, according to previous studies, the coupling of a cell adhesion peptide into PPF matrices for use as scaffold for tissue regeneration requires hydrophilic spacers. Because the hydrophilic spacers tend to reduce the desired mechanical properties of the resulting polymer, a method for modifying PPF to include one or more peptides without the need for hydrophilic spacers is desired.

SUMMARY OF THE INVENTION

The present invention includes a novel method to tether PEG to PPF ends for peptide coupling without changing the molecular weight distribution of the PPF block. The present method utilizes bis-carboxymethyl PEG (PEG-COOH), since the carboxyl group can be readily transformed to a highly reactive acid chloride. PEG-carbonyl chloride (PEG-COCl) reacts readily with PPF and forms PPF copolymer with PEG end blocks. The remaining end carboxyl groups of PEG-tethered PPF can be used for further modification with various desired peptides, including those having osteogenic, angiogenic, or thrombogenic properties, and many other bioactive compounds. This novel method is valuable for the preparation of PPF copolymer with PEG end groups and its modification for biological purposes.

BRIEF DESCRIPTION OF THE DRAWINGS

For a better understanding of the present invention, reference will be made to the attached Figures, wherein:

FIGS. 8A–E are FT-IR spectra of PPF, PEG-tethered PPF, succinimidyl ester of PEG-tethered PPF, modified PEG-tethered PPF with glutamine, and modified PEG-tethered PPF with GRGD, respectively.

DETAILED DESCRIPTION OF A PREFERRED EMBODIMENT

The present invention includes a novel method for tethering PEG to PPF ends for peptide coupling without changing the molecular weight distribution of the PPF block. One preferred method utilizes bis-carboxymethyl PEG (PEG-COOH), since the carboxyl group can be easily transformed to a highly reactive acid chloride. PEG-carbonyl chloride (PEG-COCl) reacts readily with PPF and forms PPF copolymer with PEG end blocks. The remaining end carboxyl groups of PEG-tethered PPF can be used for further modification with cell adhesion peptides or the like.

Preparation of PPF

PPF is preferably prepared by the method described in co-pending application Ser. No. PCT/US99/07912, filed Apr. 9, 1999, and entitled "Synthesis of Poly (Proplyene Fumarate) by Acylation of Propylene Glycol in the Presence of a Proton Scavenger," which is incorporated herein by reference, with minor modification. The reaction is believed to proceed according to the mechanism shown in FIG. 1. Briefly, oligo(propylene fumarate) is obtained by dropwise addition of fumaryl chloride into a three-neck round bottomed flask charged with propylene glycol, potassium carbonate, and methylene chloride. A preferred ratio of fumaryl chloride to propylene glycol and potassium carbonate is 1:3:2.5. In one embodiment, fumaryl chloride is added to a solution of propylene glycol in methylene chloride at 0° C. under nitrogen. After addition of the fumaryl chloride, the reaction mixture is stirred for an additional 2 h at 0° C., followed by the addition of water to remove the remaining propylene glycol and potassium carbonate. The organic phase is separated and is dried with anhydrous sodium sulfate. After solvent removal by rotovaporation, the molecular weight of the oligomer is increased by transesterification at 160° C. at 0.25 torr. Hydroquinone is preferably added to prevent thermal cross linking at this point. Transesterification is preferably performed for about 12 hr and the molecular weight change is monitored by gel permeation chromatography using polystyrene standards for a relative calibration curve. The resulting PPF can be purified through solution precipitation in chloroform and petroleum ether.

Tethering PPF with PEG

Figure 1:
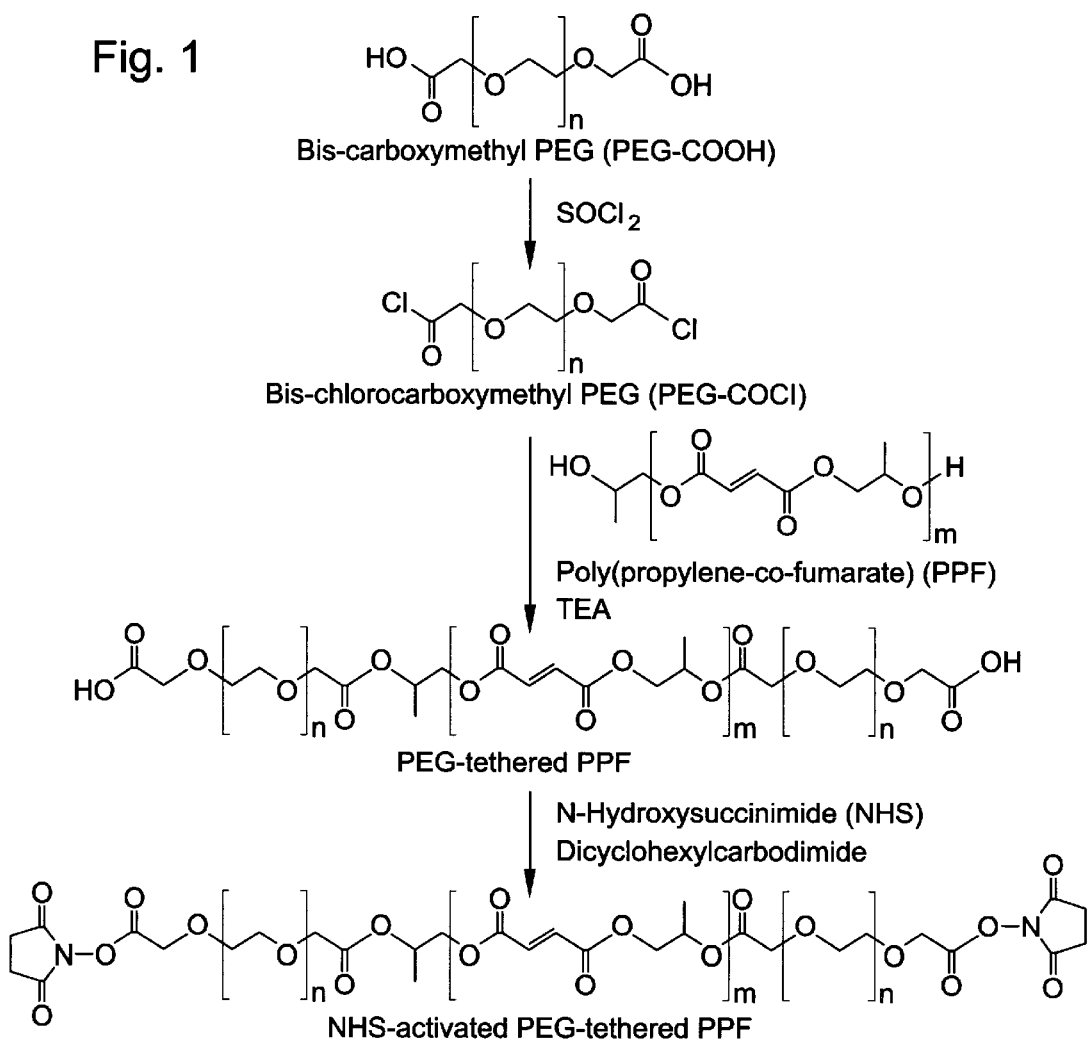
FIG. 1 is a schematic chemical diagram illustrating the synthetic reactions for tethering PEG to PPF and preparing the succinimidyl ester of PEG-tethered PPF for peptide attachment.

Purified PPF (Mn=2900) is tethered with PEG as illustrated in FIG. 1. A preferred method for tethering PPF to PEG is as follows. PEG-COOH is first dried by azeotropic distillation out of anhydrous benzene. Thionyl chloride is added to the residual PEG-COOH and the solution is stirred overnight at 70° C. to form PEG-COCl. The remaining thionyl chloride is removed by distillation under reduced pressure and further removed by distilling after adding additional anhydrous benzene. Conversion of COOH to COCl is about 89% by NMR spectroscopy. Any alternative method for obtaining PEG-COCl can be used.

An amount of previously dried PPF and a corresponding amount of triethylamine or other suitable organic proton scavenger, or an inorganic proton scavengers such as potassium carbonate, in anhydrous methylene chloride or other non-protonic, PPF solvent are added dropwise to a 20% PEG-COCl solution in anhydrous methylene chloride in an ice bath. After stirring 6 hours at room temperature, the solvent is removed by rotovaporation and the residue is dissolved into 200 ml of deionized distilled water (DDW). After adjusting the pH of the solution to 2.0 with 1N HCl, the PPF tethered with PEG is extracted in methylene chloride. The extract is preferably neutralized with triethylamine, dried with anhydrous sodium sulfate or magnesium sulfate or other suitable drying agent, and concentrated by rotovaporation. Free PEG-COOH is preferably removed by washing several times with isopropanol. The result is PEG-tethered PPF.

Activation of PEG-tethered PPF with N-hydroxysuccinimide (NHS)

FIG. 1 further illustrates a believed mechanism for the activation of PEG-tethered PPF with N-hydroxysuccinimide. Activation causes the PEG-tethered PPF molecules to be modified such that the hydroxyl groups at both ends of the PEG-tethered PPF were substituted with NHS. According to one preferred method, PEG-tethered PPF is dried by azeotropic distillation with anhydrous benzene. After dissolving the dried PEG-tethered PPF and a corresponding amount of NHS in anhydrous methylene chloride, dicyclohexylcarbodiimide (DCC) is added to the solution. After reacting overnight at room temperature, precipitated dicyclohexyl urea is filtered out and the solution including product is concentrated by rotovaporation. NHS-activated PEG-tethered PPF is purified further by precipitation with anhydrous ether after dissolving in anhydrous ethyl acetate. The resulting activated polymer is preferably dried under vacuum and kept in a refrigerator so as to avoid decomposition.

Attachment of a biocompatible organic group to PEG-tethered PPF

Figure 2:
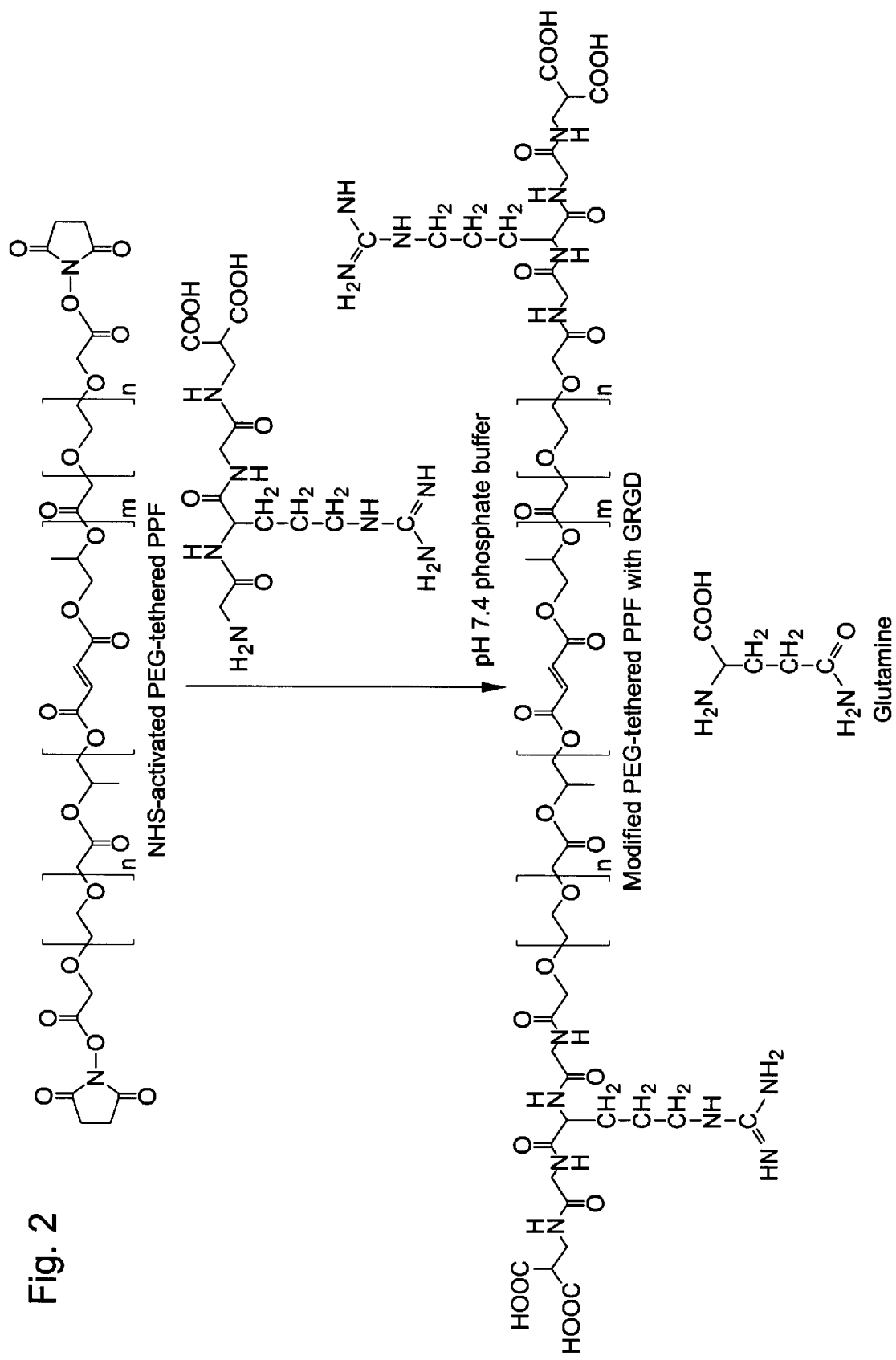
FIG. 2 is a schematic chemical diagram illustrating the reaction scheme for modifying PEG-tethered PPF with GRGD and the chemical structure of glutamine.

Proteins, protein fragments, carbohydrates, proteoglycans, glycoproteins, amino acids or peptides can be coupled to PEG-tethered PPF (and thus included in the poly(propylene fumarate-co-ethylene glycol) network) according to the representative mechanism shown in FIG. 2. One preferred method for carrying out this reaction is as follows. An amount of the desired amino acid(s) or peptide(s) is dissolved in a 50 mM pH 7.4 phosphate buffer. After likewise dissolving NHS-activated PEG-tethered PPF in anhydrous dimethylformamide, the polymer solution is preferably added dropwise to the amino acid or peptide solution in an ice bath and stirred for another 2 hr. A preferred temperature range for this reaction is between 0° C. and room temperature. If the temperature is too low, the peptide solution may freeze, and the reaction will be much slower. Excessively high temperatures may cause side reactions and thus lower the reaction yields. The solution is preferably transferred to a dialysis membrane and dialyzed using deionized distilled water to remove unreacted peptide. Alternatively, the unreacted peptide can be removed by any other suitable technique. After the unreacted peptide is removed, the resulting solution of modified PPF with GRGD is immediately frozen with liquid nitrogen and lyophilized overnight so as to remove water therefrom.

Peptides that can be coupled to the activated PEG-tethered PPF include but are not limited to: RGD, YIGSR, REDV, IKVAV, and KRSR peptides. Proteins that can coupled to the activated PEG-tethered PPF include but are not limited to members of the transforming growth factor beta superfamily, including the bone morphogenetic proteins, as well as basic fibroblast growth factor, platelet derived growth factor, and insulin like growth factor. Other examples include extracellular matrix molecules such as osteo-pontin, osteonectin, osteocalcin, and bone sialoprotein. Protein fragments that can coupled to the activated PEG-tethered PPF include but are not limited to any fragments of the above proteins comprising 3–30 amino acids. Hyaluronic acid is an example of a suitable proteoglycan. Carbohydrates that can coupled to the activated PEG-tethered PPF include but are not limited to: starch, cellulose, and chitin.

EXAMPLE

In order to obtain a quantity of one form of the novel composition for testing, the foregoing steps were carried out as set out in the following Example. Fumaryl chloride, propylene glycol, and calcium hydride were purchased from Acros (Pittsburgh, Pa.) and used after distillation. Thionyl chloride (2 M in methylene chloride), bis-carboxymethyl PEG (Mn=600), triethylamine, N-hydroxysuccinimide (NHS), dicyclohexylcarbodiimide (DCC), anhydrous benzene, anhydrous dimethyl formamide, glutamine, trinitrobenzene sulfonic acid (TNBS), glycine-arginine-glycine-aspartic acid (GRGD), and various solvents were purchased from commercial sources. (Torrance, Calif.). Methylene chloride for organic reactions was purified by distillation after refluxing 4 hr over calcium hydride.

Thirty grams of PEG-COOH of molecular weight 600 were dried by azeotropic distillation of 100 ml out of 150 ml of anhydrous benzene. After adding 0.1 mole of thionyl chloride to the residual PEG-COOH, the solution was stirred overnight at 70° C. to form PEG-COCl. The remaining thionyl chloride was removed by distillation under reduced pressure and further removed by distilling after adding another 60 ml of anhydrous benzene. Conversion of COOH to COCl was about 89 % by NMR spectroscopy.

Twenty grams of previously dried PPF having a number average molecular weight of 2900 (manufactured according to known techniques) and 16 ml of triethylamine in 100 ml of anhydrous methylene chloride are added dropwise to 20% PEG-COCl solution in anhydrous methylene chloride in an ice bath. After stirring 6 hours at room temperature, the solvent was removed by rotovaporation and the residue was dissolved into 200 ml of deionized distilled water (DDW). After adjusting the pH of the solution to 2.0 with 1N HCl, the tethered PPF with PEG was extracted in three 200 ml portions of methylene chloride. The extract was neutralized with triethylamine, dried with 20 g of anhydrous sodium sulfate, and concentrated by rotovaporation. Free PEG-COOH was removed by washing several times with isopropanol. 16.18 g of PEG-tethered PPF were obtained.

Sixteen grams of the PEG-tethered PPF were dried by azeotropic distillation with 100 ml of anhydrous benzene. After dissolving the PEG-tethered PPF and 3.0 g of NHS (0.026 mole) in 150 ml of anhydrous methylene chloride, 7.0 g of DCC (0.034mole) were added. After reacting overnight at room temperature, precipitated dicyclohexyl urea was filtered out and the solution including product was concentrated by rotovaporation. NHS-activated PEG-tethered PPF was purified further by precipitation with anhydrous ether after dissolving in 100 ml of anhydrous ethyl acetate. Activated polymer was dried under vacuum and kept in a refrigerator.

Five milligrams of glutamine or GRGD were dissolved in 3.5 ml of 50 mM pH 7.4 phosphate buffer. After dissolving 270 or 55 mg of NHS-activated PEG-tethered PPF in 1.5 ml of anhydrous dimethylformamide for glutamine and GRGD respectively, the polymer solution was added dropwise to the amino acid or peptide solution in an ice bath and stirred for another 2 hr. The solution was transferred into a regenerated cellulose ester dialysis membrane (MWCO=2000, Spectrum) and dialyzed by using deionized distilled water for 2 days with periodic medium changes. After dialysis, the solution of modified PPF with GRGD was immediately frozen with liquid nitrogen and lyophilized overnight. GRGD coupling to PPF was characterized by $H^1$-NMR (Bruker AC 250 NMR spectrometer) after dissolving in $D_2O$—$CD_3OD$ (1:2) solution. Coupling of glutamine and GRGD is analyzed by using the TNBS method established by Snyder and Sobocinsky.

Characterization of Polymer and Modified Polymer

FT-IR spectra are obtained on a Nicolet 500 spectrometer (Madison, Wis). Samples are dissolved in $CDCl_3$ and placed on a calcium fluoride window (Aldrich, Milwaukee, Wis.). After forming a thin film by evaporating solvent with nitrogen gas, sixteen scans are collected at a 4 $cm^{-1}$ resolution by using the calcium fluoride window as a reference. NMR spectra are obtained on Bruker AC 250 using $CDCl_3$, $D_2O$, $CD_3D$, and pyridine-$d_5$ as solvents. Proton NMR spectra of GRGD and glutamine are recorded in $D_2O$ while those of modified PEG-tethered PPF with GRGD and glutamine are in $D_2O$-pyridine-$d_5$ (8:2) and $D_2O$—$CD_3OD$ (1:2) solutions respectively since the solubility in a single solvent is apparently low.

Gel permeation chromatography is used to characterize PPF and PEG-tethered PPF. A Phenogel guard column (50×7.8 mm, 5 μmm, mixed bed, Phenomenex, Torrance, Calif.) and a Phenogel column (50×7.8 mm, 5 μm, mixed bed, Phenomenex) are used to elute the samples at 1 ml/min chloroform flow rate. Polystyrene standards are used to obtain a calibration curve for calculating the polymer molecular weight.

Results and Discussion

A flexible PEG chain is especially valuable when the PEG chain is employed as spacer to attach bioactive molecules such as peptides and proteins. For effective coupling of those molecules into polymeric substrates, the hydrophilic PEG chain(s) should be tethered as end blocks. In the present system, tethered PEG chains may also facilitate the specific interaction between ligand and ligate.

The particular peptide sequence plays a ubiquitous role on cell adhesion process. The peptide sequence arginine-glycine-aspartic acid (RGD) has been established as a minimal peptide sequence responsible for integrin/ligand interaction on many adhesive proteins such as fibronectin, vitronectin, collagen, and laminin. Therefore, synthetic RGD peptides have been immobilized into polymeric materials to improve specific cell attachment. Cook et al modified poly(lactic acid-co-lysine) with RGD peptide for possible application as a temporary scaffold for cell transplantation.

Hem and Hubbell incorporated RGD-peptide sequences into PEG diacrylate networks by photopolymerization and reported that RGD peptide required a certain hydrophilic spacer for specific cell spreading into nonadhesive PEG diacrylate matrices.

PPF Formation

Figure 3:
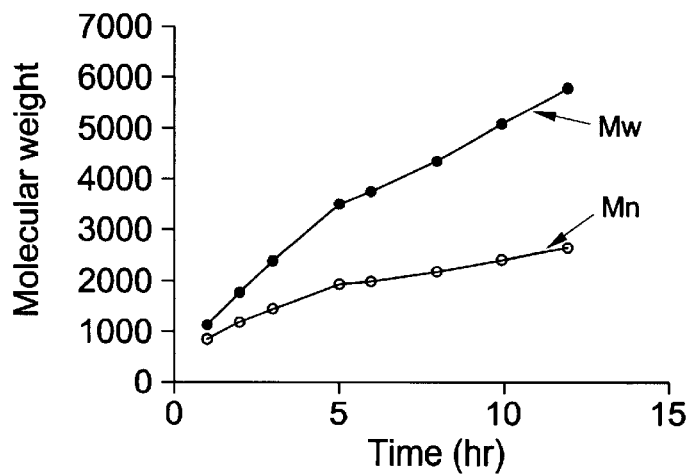
FIG. 3 shows representative plots of the increase of number-average molecular weight (Mn) and weight-average molecular weight (Mw) versus time during a transesterification.

For tethering PEG, PPF is prepared by the transesterification of oligo(propylene fumarate). The number-average molecular weight (Mn) of PPF increased up to about 2900 while the weight-average molecular weight (Mw) went up to 5300 (FIG. 3). The Mn of the PPF is also determined by end-group analysis with NMR spectroscopy after reacting end hydroxyl groups with trifluroacetic anhydride as 2700. (The value determined by GPC is used in the molar ratio calculation.) During the transesterification, a main variable determining molecular weight is time. The temperature is kept below 200° C. to prevent side reactions such as spontaneous cross linking and addition to fumarate double bonds. By proton NMR spectroscopy, methyl, methylene, and methine proton peaks from propylene glycol appeared at 1.3, 4.2, and 5.3 ppm respectively (data not shown but available from the NMR spectrum of PEG-tethered PPF in FIG. 4C). The NMR spectrum of prepared PPF is consistent with those reported previously.

Preparation of PPF and PEG tethering

Figure 4:
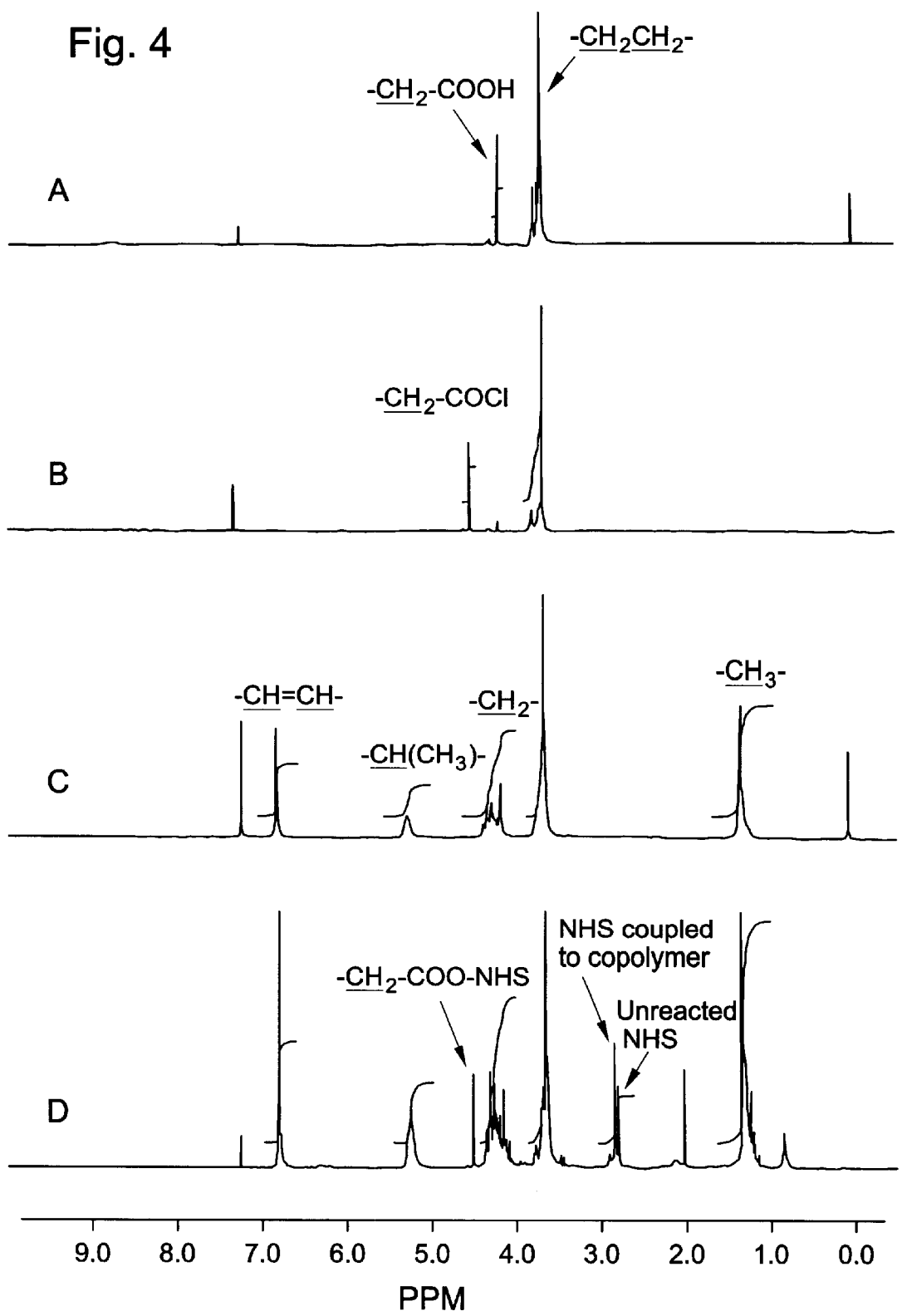
FIGS. 4A–D show proton NMR spectra of bis-carboxymethyl PEG (PEG-COOH), PEG-COCl, PEG-tethered-PPF, and succinimidyl ester of PEG-tethered PPF in CDCl$_3$, respectively.

Before tethering PEG to PPF, PEG-COOH is transformed into reactive PEG-COCl, as shown in FIG. 1. It has been found that the carboxyl groups of PEG-COOH are easily converted to the highly reactive acid chloride (—COCl) by reaction with thionyl chloride. FIG. 4-B shows the change in the NMR spectrum of PEG-COOH upon reaction with thionyl chloride. As FIG. 4-A and B show, a methylene (—$\underline{CH_2}$—COOH) proton peak shifted from 4.1 ppm to 4.5 ppm upon replacement of OH by the electron-withdrawing chloride. The areas under the peaks indicate that the conversion is 89%.

PEG-COOH of molecular weight 600 and 250 are commercially available. PEG of other molecular weights also can be tethered to PPF after converting PEG to PEG-COOH by known methods. Alternatively, instead of modifying the functionality of PEG, the functionality of the PPF can be changed to an acid chloride by first carboxylating PPF with succinic anhydride. This alternative is disadvantageous, however, inasmuch as the ester bonds of PPF are labile to thionyl chloride. In a preferred embodiment, prepared PEG-COC of molecular weight 600 is reacted with PPF in the presence of triethylamine.

Figure 5:
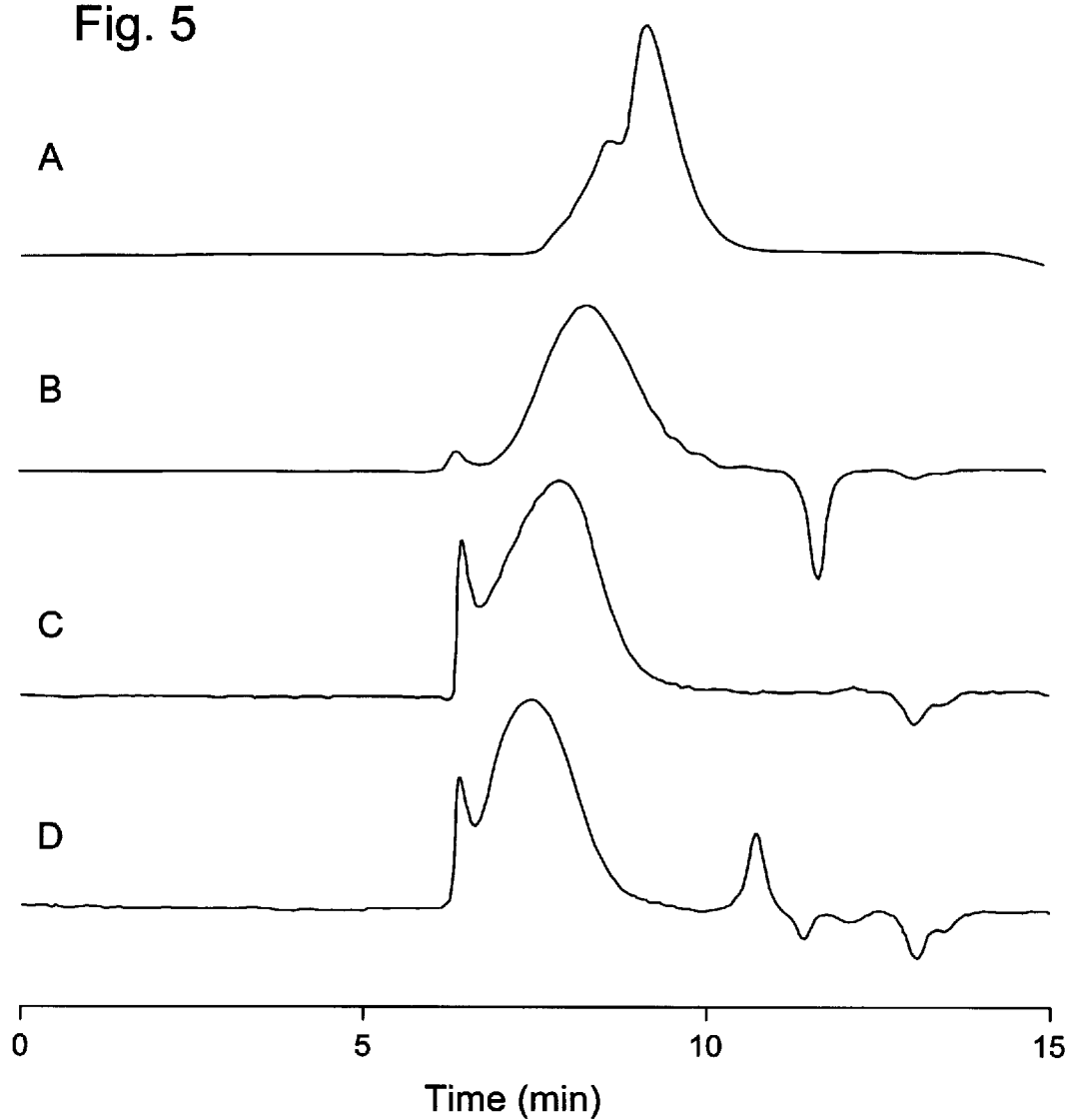
FIGS. 5A–D are GPC chromatograms of PEG-COOH, PPF, PEG-tethered PPF, and succinimidyl ester of PEG-tethered PPF, respectively.

As shown in FIG. 4-C, significant proton peaks from PEG appeared at 3.6 ppm, in addition to proton peaks from PPF as a result of PEG tethering. According to integration of methyl (—$\underline{CH_3}$) peaks of PPF and methylene (—$\underline{CH_2}$ $\underline{CH_2}$—) proton peaks from PEG, more than two PEG blocks are tethered to PPF. On the basis of the molecular weight of PPF (Mn=2900), molecular weight of PPF repeating unit (Mr=155) and PEG-COOH (Mn=600), ratios of PEG methylene proton to PPF methyl protons of PEG-PPF-PEG triblock copolymer and PEG-PPF diblock copolymer should be about 2:1 and 1:1, respectively. From the NMR spectrum of PEG-tethered PPF, the proton ratio is 2.6:1. The main reason for the difference in proton ratios between the predicted triblock copolymer and the obtained copolymer might be the molecular weight distribution of PEG-COOH and possible overestimation of molecular weight of PPF. As seen in FIG. 5, the molecular weight distribution of commercially available PEG-COOH of molecular weight 600 is not nor mal. However, relative molecular weights from Table 1 strongly supported the formation of PEG-PPF-PEG triblock copolymer.

TABLE 1

Molecular weights obtained by GPC.

|  | Mn* | Mw* |
| --- | --- | --- |
| Bis-carboxymethyl PEG 600 | 1300 | 2000 |
| PPF | 2900 | 5300 |
| PEG-tethered PPF | 5900 | 9900 |
| Succinimidyl ester of PEG tethered PPF | 7600 | 11600 |

*Number-average molecular weight (Mn) and weight-average molecular weight (Mw) based on polystyrene standards in chloroform.

Using GPC analysis and polystyrene standards, the relative molecular weight (number-average molecular weight, Mn) of PEG-COOH and PEG-tethered PPF are 1300 and 5900 respectively. Considering the molecular weight of PPF as 2900, molecular weights of PEG-PPF and PEG-PPF-PEG would be 4200 and 5500. In comparison with calculated molecular weights of di- or tri-block copolymers, the obtained molecular weight of copolymer, 5900, is very close to that of triblock copolymer, 5500. In the chromatogram, unreacted PEG is not observed. The molecular weight of PEG-COOH is overestimated by using polystyrene standards, which might be due to different hydrodynamic behavior of PEG from polystyrene because of conformational differences. These GPC results confirmed that the PEG-PPF-PEG tri-block copolymer instead of di-block copolymer were produced by this synthetic method.

Figure 6:
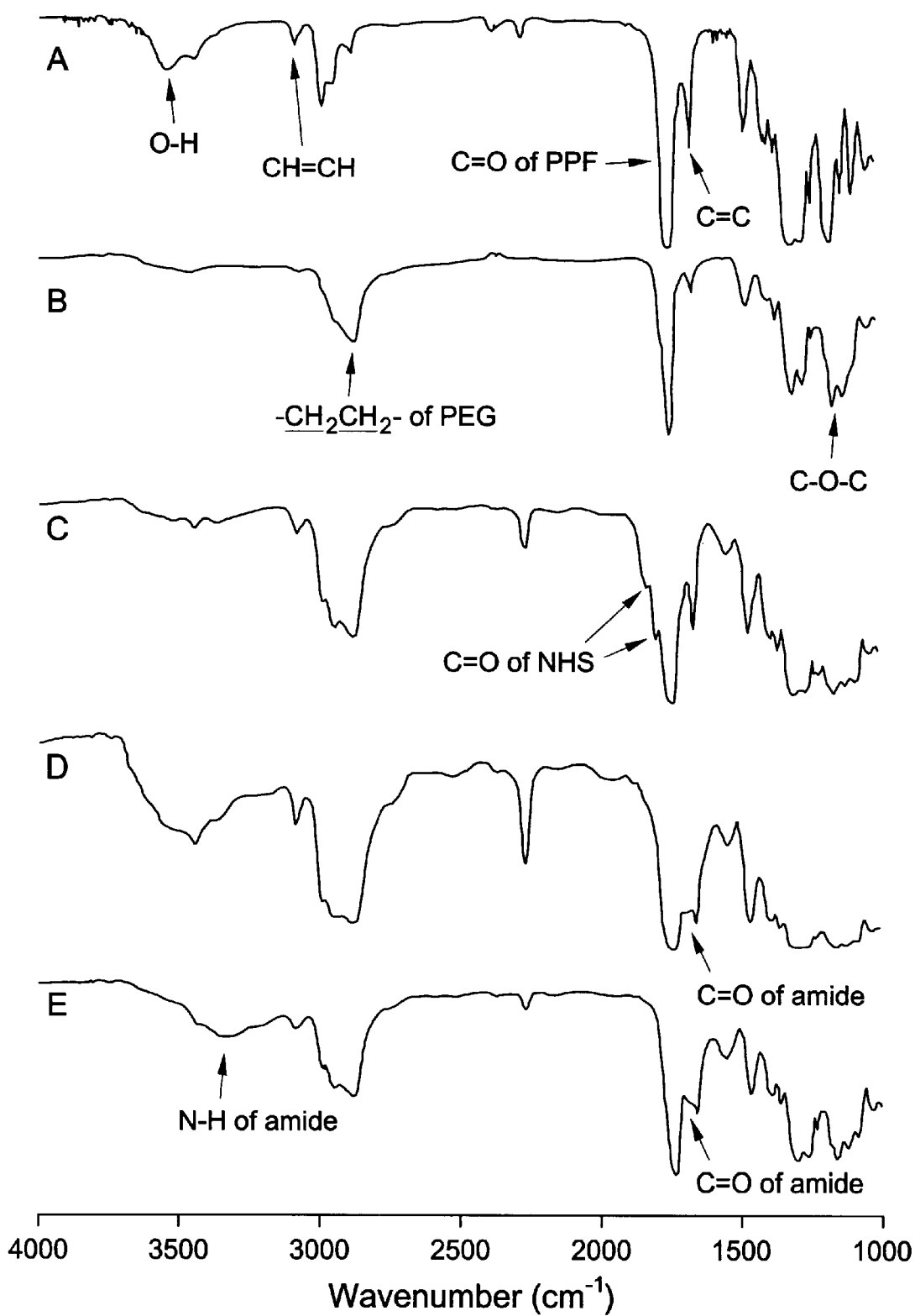
FIGS. 6A–E are FT-IR spectra of PPF, PEG-tethered PPF, succinimidyl ester of PEG-tethered PPF, modified PEG-tethered PPF with glutamine, and modified PEG-tethered PPF with GRGD, respectively.

Infrared (IR) spectra are especially valuable for the characterization of PEG-tethered PPF. The IR spectrum of PPF showed the following characteristic bands in FIG. 6-A: —OH stretch at 3400 $cm^{-1}$, C—H stretch of —CH=CH— at 3080 $cm^{-1}$, ester carbonyl at 1720 $cm^{-1}$, and — C=C stretch at 1646 $cm^{-1}$. After tethering PEG to PPF, spectral changes are observed as seen in FIG. 6-B: disappearing —OH band at 3400 $cm^{-1}$, building up more C—H stretching band at 2870 $cm^{-1}$, and C—O—C stretching at 1120 $cm^{-1}$. It is apparent from these GPC and IR data that PEG is successfully tethered to PPF.

In the reaction to prepare PEG-tethered PPF, the preferred molar ratio of PEG-COCl to PPF is 7.2:1. Taking into consideration the conversion of PEG-COOH into PEG-COCl, the ratio of reactive functional groups between —COCl and —OH is 6.4:1. It is preferred to employ an excess amount of PEG-COCl, so as to prevent the formation of copolymer with more than two PPF blocks. To prepare PPF copolymer with PEG end blocks, PPF should be added into PEG-COCl solution, since the opposite order of addition is more likely form copolymer of more than two PPF blocks.

One important advantage for this method of preparation of poly(propylene fumarate-co-ethylene glycol) (P(PF-co-EG)) is that reaction occurs only at the end hydroxyl groups of PPF. Therefore, this method does not alter the molecular weight distribution of the PPF block, as does transesterification. Using the reaction scheme presented in FIG. 1, PEG-PPF-PEG triblock copolymer also can be prepared by using monomethoxy-PEG (m-PEG). m-PEG can be converted into m-PEG-COOH by the same method for the preparation of PEG-COOH. The method employed here is versatile enough to modify other polymers with hydroxyl groups including but not limited to poly(hydroxyethyl methacrylate), poly(vinyl alcohol), poly caprolactone diol, polybutadiene diol, and even celluose derivatives.

The type of tri-block copolymers prepared according to the present techniques are valuable for biological applications, since tethered PEG improved the solubility and biocompatibility of PPF or other polymers. Moreover, end-tethered PEG blocks of a copolymer retain high flexibility that helps to prevent protein adsorption on the basis of steric repulsion. PEG end blocks are especially valuable as flexible spacers for immobilization of biological molecules such as peptides and proteins. For the coupling of such molecules, certain functional groups are necessary. In the case of the copolymer obtained from PEG-COOH, the remaining end carboxyl groups can be converted directly to the necessary functional groups.

The PEG-tethered PPF is activated with NHS in the presence of DCC at room temperature. In FIG. 4D, the NMR spectrum of the N-hydroxysuccinimidyl ester of PEG-tethered PPF showed a proton peak of succinimide at 2.83 ppm in addition to proton peaks from PPF and PEG. Another noticeable change in the NMR spectrum is the shift of the methylenecarboxy protons from 4.1 to 4.5 ppm because of the succinimidyl group. A singlet at 2.78 ppm represents the presence of unreacted N-hydroxysuccinimide, which can not be completely removed even by precipitation from dry ethyl acetate by ethyl ether. FIG. 5-C shows the GPC chromatogram of the succinimidyl ester of PEG-tethered PPF. Comparing with PEG-tethered PPF, the molecular weight distribution of the activated copolymer shifted toward higher values, possibly because NHS attached to both ends and the purification process removed low molecular weight copolymer. The obtained molecular weight of succinimidyl ester of PEG-tethered PPF by GPC is 7600, which is significantly higher than that of PEG-tethered PPF of 5900. However, the shape of the molecular weight distribution of the copolymer is close to that of PPF even after purification (FIG. 5-C).

Figure 7:
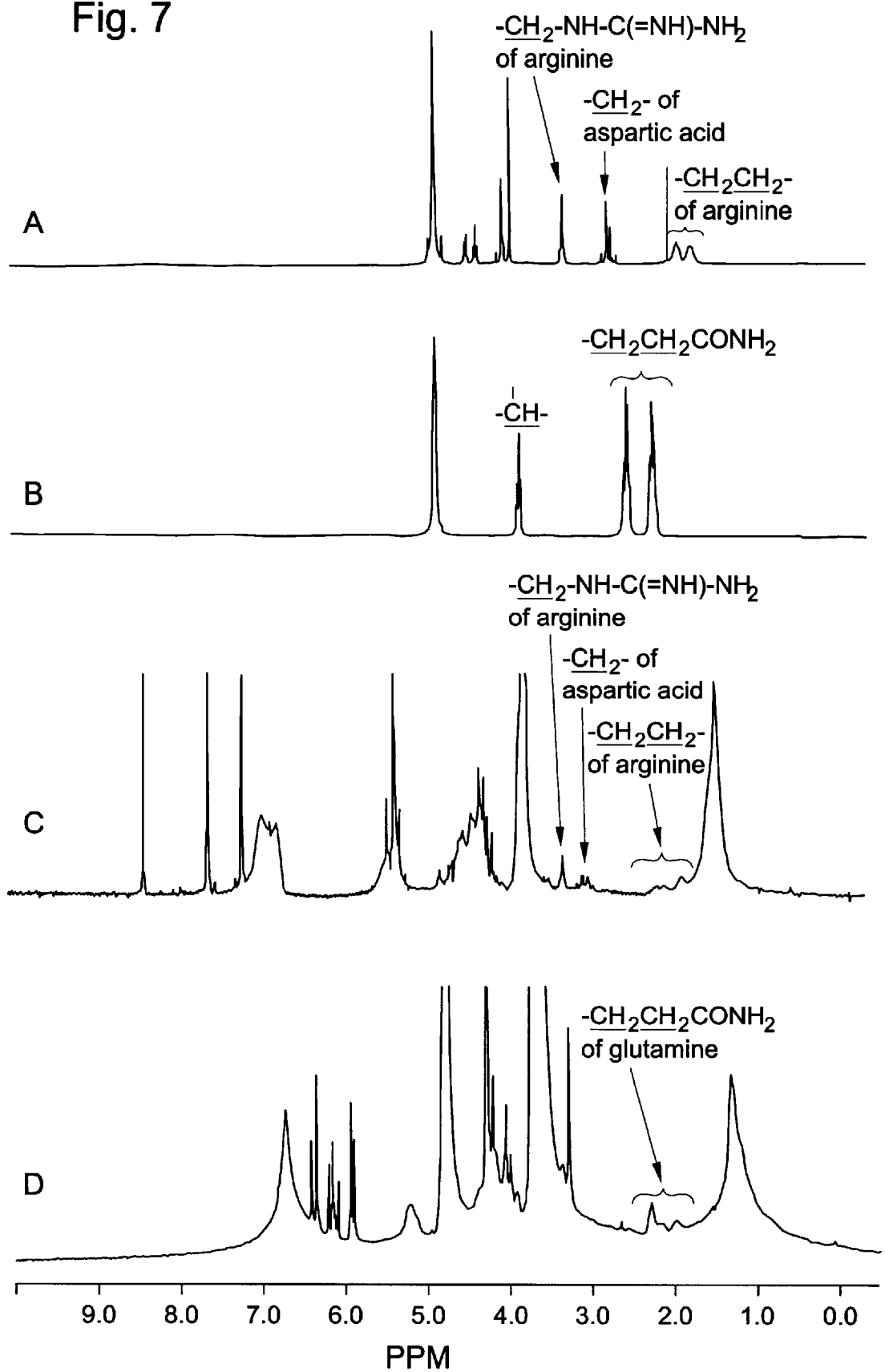
FIGS. 7A–D are proton NMR spectra of GRGD and glutamine in D$_2$O and PEG-tethered PPF with GRGD in D$_2$O-pyridine-d$_5$ (8:2) and glutamine in D$_2$O—CD$_3$D (1:2), respectively.

The N-hydroxysuccinimidyl ester of the copolymer is used for the coupling of glutamine and GRGD without further purification, since the small amount of remaining NHS does not affect the coupling reaction in a buffered solution. Because PPF with carboxymethyl-NHS is highly reactive, glutamine and GRGD are attached to this copolymer at pH 7.4. Normally, the pH for aminolysis using N-hydroxysuccinimidyl ester of PEG succinate ranges from 8.0 to 9.0. The higher reactivity toward amines of carboxymethyl-NHS than succinyl-NHS to amines required lowering the pH of the reaction medium. After coupling glutamine and GRGD to PEG-tethered PPF, characteristic proton peaks from glutamine and GRGD are observed in the NMR spectra. Mixtures of $D_2O$ and $CD_3OD$ (1:2) and $D_2O$-pyridine-$d_5$ (4:1) are used as solvent for NMR spectroscopy because the modified copolymers are not readily soluble in a single solvent. As seen in FIG. 7-D, the NMR spectrum of PEG-tethered PPF modified with glutamine showed broad multiplets of glutamine (—$\underline{CH_2}$—$\underline{CH_2}$—C(O)$NH_2$) ranging from 1.8 to 2.5 ppm. After coupling GRGD onto the polymer, three distinct proton peaks from the peptide are identified in NMR spectrum. These peaks are broad multiplets because of the —$\underline{CH_2}$—$\underline{CH_2}$—$\underline{CH_2}$—NH—C(=NH)—$NH_2$ group of arginine ranging from 1.5 to 2.0 ppm, a multiplet of $\underline{CH_2}$—COOH of aspartic acid at 2.8 ppm, and a triplet of —$CH_2$—$CH_2$—$\underline{CH_2}$—NH—C(=NH)—$NH_2$ of arginine at 3.1 ppm (FIG. 7C). The proton peaks are assigned on the basis of the NMR spectra of GRGD and glutamine in $D_2O$ that are presented in FIGS. 7A and 7B. Glutamine is chosen as a model amino acid for the modification of PEG-tethered PPF because it has proton peaks from the side group that do not overlap with those of the PPF copolymer.

Modified PEG-tethered PPF is characterized by IR spectroscopy in addition to NMR spectroscopy. In comparison with the IR spectrum of PEG-tethered PPF (FIG. 6-B), that of copolymer modified with glutamine and GRGD showed differences in the N—H stretching region (from 3100 to 3450 $cm^{-1}$) and carbonyl stretching region (from 1600 to 1800 $cm^{-1}$) (FIGS. 6D and 6E). Copolymers modified with glutamine and GRGD showed characteristic N—H stretching bands ranging from 3100 to 3450 $cm^{-1}$ attributed to the amide bonds formed between end carboxylic acid groups and the amine group of glutamine or GRGD. The N—H stretching band of the copolymer modified with GRGD is broad but more readily identifiable than that of the copolymer modified with glutamine because the modification with the peptide resulted in four amide bonds. FIG. 8 shows expanded carbonyl stretching bands of copolymer with or without modification by glutamine and GRGD. The change in the carbonyl stretching region is more obvious in FIG. 8 than in FIG. 6. IR spectra of modified copolymers with glutamine and GRGD showed carbonyl stretching bands, amide I bands, that ranged from 1660 to 1720 $cm^{-1}$. The amide I bands partially overlapped with the carbonyl stretching (1720 $cm^{-1}$) and —C=C stretching band 1646 $cm^{-1}$) of PPF. IR spectral changes in both regions also indicated a successful coupling of glutamine and GRGD to PEG-tethered PPF.

However, NMR spectra presented in FIGS. 7 are only qualitative, since the polymeric proton peaks are broadened. For the quantitative analysis of the coupling, unreacted amino groups are analyzed by using trinitrobenzene sulfonic acid (TNBS). Calculated yields of coupling according to TNBS analyses are 90 and 99% for glutamine and GRGD, respectively. Based on the work by Hem and Hubbell, these results are reasonably acceptable. They reported that the succinimidyl ester of acryloyl PEG of molecular weight 3400 could couple tyrosine-arginine-aspartic acid-glycine-serine (YRDGS) with 85% yields according to a primary amine analysis with fluoroaldehyde. Higher yields with GRGD and glutamine than with YRDGS can be explained by a reduced steric hindrance for the amino groups of glutamine and glycine than tyrosine. The analysis with TNBS could also lead to a higher estimation, on account of interference by coexisting substances. However, the control reactions with DMF and N-hydroxysuccinimide did not cause any apparent change in UV absorbance at the wavelength for quantification, 420 nm. PPF did not show any significant UV absorbance at 420 nm at the concentration of copolymer for quantification. Thus, both spectroscopic characterization and quantitative analysis of unreacted amino groups with TNBS indicated an effective coupling of glutamine and GRGD. The presence of trace amount of free peptide or amino acid even after purification by dialysis is only a minor concern.

The activated, succinimidyl ester of PEG-tethered PPF described herein can be modified by other bioactive molecules, including proteins. For example, a modified PEG-tethered PPF with a cell adhesion peptide can be useful for the preparation of polymeric scaffolds for tissue regeneration. The peptides that remain incorporated after in situ polymerization of the fumarate double bonds will be effective for the specific cell attachment on the scaffold. The hydrophilic flexible PEG spacer will facilitate the interaction of cells with peptides. On the basis of high mechanical strength of PPF matrices, copolymer modified with peptides that are specific to bone cells will be valuable for bone and dental tissue engineering.

Conclusions

PEG, a highly biocompatible polyether, is tethered to PPF, a biodegradable polyester, by using bis-carboxymethyl PEG. Tethered PPF can be activated to couple a cell adhesion peptide or other active molecule. GRGD, a model peptide, can be attached to PEG-tethered PPF. The peptide coupled to the end of PEG-tethered PPF can be incorporated into polymeric scaffolds by in situ polymerization, since the PPF block has polymerizable fumarate double bonds.

What is claimed is:

1. Poly(propylene fumarate) modified with a biocompatible organic group selected from the group consisting of peptides, proteins, protein fragments, proteoglycans, glycoproteins, and carbohydrates.

2. The poly(propylene fumarate) according to claim 1 wherein the peptide is selected from the group consisting of RGD, YIGSR, REDV, IKVAV, and KRSR peptides.

3. The poly(propylene fumarate) according to claim 1 wherein the protein is selected from the group consisting of members of the transforming growth factor beta superfamily, bone morphogenetic proteins, basic fibroblast growth factor, platelet derived growth factor, insulin like growth factor, and extracellular matrix molecules including osteopontin, osteonectin, osteocalcin, and bone sialoprotein.

4. The poly(propylene fumarate) according to claim 1 wherein the protein fragments comprise fragments of the proteins selected from the group consisting of members of the transforming growth factor beta superfamily, bone morphogenetic proteins, basic fibroblast growth factor, platelet derived growth factor, insulin like growth factor, and extracellular matrix molecules including osteopontin, osteonectin, osteocalcin, and bone sialoprotein, comprising 3–30 amino acids.

5. The poly(propylene fumarate) according to claim 1 wherein the carbohydrate is selected from the group consisting of starch, cellulose, and chitin.

6. A poly(propylene fumarate) network modified with a biocompatible organic group selected from the group consisting of peptides, proteins, protein fragments, proteoglycans, glycoproteins, and carbohydrates.

7. The poly(propylene fumarate) network according to claim 6 wherein the peptide is selected from the group consisting of RGD, YIGSR, REDV, IKVAV, and KRSR peptides.

8. The poly(propylene fumarate) network according to claim 6 wherein the protein is elected from the group consisting of members of the transforming growth factor beta superfamily, bone morphogenetic proteins, basic fibroblast growth factor, platelet derived growth factor, insulin like growth factor, and extracellular matrix molecules including osteopontin, osteonectin, osteocalcin, and bone sialoprotein.

9. The poly(propylene fumarate) network according to claim 6 wherein the protein fragments comprise fragments of the proteins selected from the group consisting of members of the transforming growth factor beta superfamily, bone morphogenetic proteins, basic fibroblast growth factor, platelet derived growth factor, insulin like growth factor, and extracellular matrix molecules including osteopontin, osteonectin, osteocalcin, and bone sialoprotein, comprising 3–30 amino acids.

10. The poly(propylene fumarate) network according to claim 6 wherein the carbohydrate is selected from the group consisting of starch, cellulose, and chitin.

11. Poly(propylene fumarate-co-ethylene glycol) modified with a biocompatible organic group selected from the group consisting of peptides, proteins, protein fragments, glycoproteins, and carbohydrates.

12. The poly(propylene fumarate-co-ethylene glycol) according to claim 11 wherein the peptide is selected from the group consisting of RGD, YIGSR, REDV, IKVAV, and KRSR peptides.

13. The poly(propylene fumarate-co-ethylene glycol) according to claim 11 wherein the protein is selected from the group consisting of members of the transforming growth factor beta superfamily, bone morphogenetic proteins, basic fibroblast growth factor, platelet derived growth factor, insulin like growth factor, and extracellular matrix molecules including osteopontin, osteonectin, osteocalcin, and bone sialoprotein.

14. The poly(propylene fumarate-co-ethylene glycol) according to claim 11 wherein the protein fragments comprise fragments of the proteins selected from the group consisting of members of the transforming growth factor beta superfamily, bone morphogenetic proteins, basic fibroblast growth factor, platelet derived growth factor, insulin like growth factor, and extracellular matrix molecules including osteopontin, osteonectin, osteocalcin, and bone sialoprotein, comprising 3–30 amino acids.

15. The poly(propylene fumarate-co-ethylene glycol) according to claim 11 wherein the carbohydrate is selected from the group consisting of starch, cellulose, and chitin.

16. A poly(propylene fumarate-co-ethylene glycol) network modified with a biocompatible organic group selected from the group consisting of peptides, proteins, protein fragments, proteoglycans, and carbohydrates.

17. The poly(propylene fumarate-co-ethylene glycol) network according to claim 16 wherein the peptide is selected from the group consisting of RGD, YIGSR, REDV, IKVAV, and KRSR peptides.

18. The poly(propylene fumarate-co-ethylene glycol) network according to claim 16 wherein the protein is selected from the group consisting of members of the transforming growth factor beta superfamily, bone morphogenetic proteins, basic fibroblast growth factor, platelet derived growth factor, insulin like growth factor, and extracellular matrix molecules including osteopontin, osteonectin, osteocalcin, and bone sialoprotein.

19. The poly(propylene fumarate-co-ethylene glycol) network according to claim 16 wherein the protein fragments comprise fragments of the proteins selected from the group consisting of members of the transforming growth factor beta superfamily, bone morphogenetic proteins, basic fibroblast growth factor, platelet derived growth factor, insulin like growth factor, and extracellular matrix molecules including osteopontin, osteonectin, osteocalcin, and bone sialoprotein, comprising 3–30 amino acids.

20. The poly(propylene fumarate-co-ethylene glycol) network according to claim 16 wherein the carbohydrate is selected from the group consisting of starch, cellulose, and chitin.

21. A method of making a PEG-tethered PPF coupled to a biocompatible organic group, comprising:

(a) providing a PPF;

(b) forming a PEG-tethered PPF by reacting the PPF with a with an activated PEG derivative; and (c) activating the PEG-tethered PPF; and (d) coupling a peptide or a protein to the activated PEG-tethered PPF.

22. The method according to claim 21 wherein step (b) comprises dissolving dried PEG-tethered PPF and a corresponding amount of N-hydroxysuccinimide in anhydrous methylene chloride and adding dicyclohexylcarbodiimide (DCC) to the solution.

23. The method according to claim 21 wherein step (a) comprises forming di(2-hydroxylpropyl) fumarate by the reaction of fumaryl chloride with propylene glycol.

24. The method according to claim 21 wherein biocompatible organic group is selected from the group consisting of peptides, proteins, protein fragments, proteoglycans, glycoproteins, and carbohydrates.

* * * * *